United States Patent [19]

Sims

[11] Patent Number: 4,906,451

[45] Date of Patent: Mar. 6, 1990

[54] INDOLE STAINS

[76] Inventor: Joel K. Sims, 2472 Waiomao Rd., Honolulu, Hi. 96816

[21] Appl. No.: 67,881

[22] Filed: Jun. 30, 1987

[51] Int. Cl.$^4$ .......................... G01N 1/00; G01N 1/30; G01N 31/00; G01N 33/48

[52] U.S. Cl. ......................................................... 424/3

[58] Field of Search ............................................ 424/3

[56] References Cited

PUBLICATIONS

Annals of Emergency Medicine, vol. 16, No. 9 (1987).
Robinson, B.; The Fisher Indole Synthesis, Wiley, New York, 1982, pp. 295, 297.
Theory and Practice of Histological Techniques; Ed. J. P. Bancroft and Stevens, New York: Churchill Livingstone, 1977, p. 115.
Arch. Perm, 84:720-732 (1961).
Hawaii Med. J., 40:243-248 (1981).
Revision of the Classification of the Oscillatoriaceal, by F. Drouet, Monograph 15, Academy of Natural Sciences of Philadelphia, Lancaster, PA: Fulton Press, pp. 224-308, 338-341 (1968).
Hawaii Med. J., 41:200-201 (1982).
Science, 196:538-540 (1977).
Science, 204:193-195 (1979).
Cancer Letters: 12:271-277 (1981).
Proc. Natl. Acad. Sci. USA, 78:3872-3876 (1981).
J. Clin. Path, 10:56-62 (1957).
Hawaii Med. J., 19:35-36 (1959).
Properties and Reactions of Indoles, by W. A. Remers, in Houlihan, W. J. (ed): Indoles (Part 1), N.Y.: Wiley-Interscience, pp. 105-107 (1972).
Principles and Techniques of Histochemistry, by Henry Troyer, Boston: Little, Brown & Co., pp. 385, 389 & 396 (1980).
Histological Staining of Indoles in Various Strains of the Stinging Seaweed, Microcoleus Lying Byaceus—Development of a New Staining Technique for Indoles, Sims et al., Copyright #TXU 243-801 (1986).
Histological Stain for Indoles: Methods and Pigments, by J. K. Sims (1986).
Development of a New Relatively Permanent Histological Staining Technique of 2,3-Indoxyl (Indole) Compounds, Copyright #TXU 197-435 (1985).

Primary Examiner—Stanley J. Friedman
Assistant Examiner—Raymond J. Henley, III
Attorney, Agent, or Firm—Cushman, Darby & Cushman

[57] ABSTRACT

A method is discussed for staining indoles comprising staining a sample using the modified DMAB technique, and then counterstaining the stained sample using the Ziehl-Neelsen acid fast bacilli stain.

6 Claims, 5 Drawing Sheets

LYNGBYATOXIN A

OPENED LYNGBYATOXIN A (OLA)

LACTONE

INDOLE

TRYPTOPHAN

| REACTANT | POSITION | ADDUCT | |
|---|---|---|---|
| DMAB | | | |
| | 2 |  | a |
| | 2 |  | b |
| | 2 |  | c |
| | 2 |  | d |
| | N at C-II |  | e |

| REACTANT | POSITION | ADDUCT |
|---|---|---|
| OPEN LYNGBYATOXIN A (OLA) | O at C12 | f |
| | N at C11 | g |

FIG. 7

| REACTANT | POSITION | ADDUCT |
|---|---|---|
| DMAB/AFB | 1 | |

FIG. 8

INDOLE STAINS

This invention relates to a relatively permanent histological stain for certain types of indoles.

BACKGROUND OF THE INVENTION

There are many types of the organic compounds known as indoles, and a variety of indoles are important as biological compounds and as pigments. Toxic indoles are present in some organisms.

The blue green algal organism *Microcoleus lyngbyaceus* is found in marine, brackish, and fresh water environments throughout the world. This species of algae is commonly encountered in the U.S.A., Canada, the Bahamas, the U.S. Virgin Islands, Bermuda, Haiti, Cuba, Jamaica, Mexico, Panama, Brazil, Argentina, Antarctica, Kenya, Libya, Egypt, Spain, Portugal, France, the Netherlands, England, Ireland, Scotland, Sweden, Norway, Russia, Denmark, Germany, Italy, Greece, Yugoslavia, Ethiopia, Union of South Africa, Malaysia, Indonesia, Vietnam, Australia, New Zealand, the Philippines, Taiwan, the Peoples Republic of China, Japan, Tonga, the Marquesas, French Polynesia, the Marshall Islands, and many other locations. In the U.S.A., *Microcoleus lyngbyaceus* has been reported in the states of Hawaii, Florida, Washington, California, Texas, Louisiana, Mississippi, Alabama, Georgia, South Carolina, North Carolina, Virginia, Maryland, Delaware, New York, Connecticut, Rhode Island, Massachusetts, Maine, and many other states.

In the State of Hawaii, the occurrence of *Microcoleus lyngbyaceus* has been reported for the islands of Kauai, Niihau, Oahu, Molokai, Lanai, Maui, and Hawaii. Toxic varieties of *Microcoleus lyngbyaceus* have been reported for Hawaii (e.g. specimens from the islands of Kauai, Oahu, Molokai, Maui, and Hawaii) and Ceylon (now Sri Lanka).

Toxic strains of the blue-green alga (i.e. phylum Cyanophyta) *Microcoleus lyngbyaceus* (formerly classified as *Lyngbya majuscula*) have been recognized as the etiologic agent of "stinging seaweed" dermatitis, a contact dermatitis, since the late 1950's and "stinging seaweed" escharotic stomatitis since 1979. *Microcoleus lyngbyaceus* dermatitis is characterized by burning sensations, itching, stinging, erythema, papules, vesicles, blisters, swelling (i.e., edema), denuded erosions, scalded appearance, eschar formation, scarring (variable), and lymphadenopathy (variable), generally in the bathing suit area, and/or conjunctivitis and rash, swelling, and pustular folliculitis over exposed parts of the body in some.

Human patch testing, animal patch testing, force feeding of animals and the investigation of natural outbreaks of human dermatitis attributable to *Microcoleus lyngbyaceus* have been some of the primary biological methods utilized in the identification of toxic versus non-toxic algal organisms. Chemical determination of algal toxicity became possible upon the extraction and subsequent identification of aplysiatoxin (Serdula, M. et. al., *Hawaii Med. J.,* 41:200–201, 1982), debromoaplysiatoxin (Mynderse, J. S. et al., *Science,* 196:538–540, 1977), and lyngbyatoxin A (Cardellina, J. H. II et al., *Science,* 204:193–195, 1979), three irritating vesicants or blister producing agents from *Microcoleus lyngbyaceus.* As purified chemicals they produce irritation, blisters, and cutaneous pustules, and all three are suspected co-carcinogens (i.e., tumor promoters) (Nakayasu, M. et al., *Cancer Letters,* 12:271–277, 1981; Fujiki, H. et al., *Proc. Natl. Acad. Sci. U.S.A.,* 78: 3872–3876, 1981).

The identification of one of these vesicants, lyngbyatoxin A, as an indole suggested that a histological staining procedure might be able to be utilized in order to qualitatively detect this toxin or derivative(s) of the toxin. The fact that lyngbyatoxin A gave a positive Ehrlich test for indoles (Cardellina, J. H. II et al., *Science,* 204:193–195, 1979) supported this approach. It was felt to be desirable to develop a histological technique which could be utilized on a routine basis by histopathology laboratories, hospitals or otherwise, particularly including application to tissues in paraffin blocks handled in a routine fashion. The development of a histological test or a chemical test was preferable to human patch testing or animal testing for considerations of potential carcinogenicity in both systems and cost in the latter testing program. The indole moiety has been detected by using the histochemical stain of Adams (Adams, C. W. M., *J. Clin. Path.,* 10:56–62, 1957) hereby incorporated by reference. Ehrlich's reagent, or p-dimethylaminobenzaldehyde, which is used for the biochemical detection of indole derivatives, was reportedly utilized as a component to stain tissues for certain types of indoles. However, fading or loss of color can occur using this method.

The initial staining method utilized was the p-dimethylaminobenzaldehyde nitrite for tryptophane and related compounds (Adams, C. W. M., *J. Clin. Path.,* 10:56–62, 1957); and *Theory and Practice of Histological Techniques,* Ed. J. D. Bancroft and A. Stevens, New York: Churchill Livingstone, 1977, p. 115). The p-dimethylaminobenzaldehyde, or DMAB, histochemical staining method for indoles is relatively specific for 2- or 3-open or reactive indoles (e.g., tryptophan, or serotonin) in regard to a blue reaction product (Adams, C. W. M., *J. Clin. Path.,* 10:56–62, 1957). Other amino acids (e.g., histidine, tyrosine, cysteine, proline, arginine, lysine, et al., as tested (C. W. M. *J. Clin. Path.,* 10:56–62, 1957), phenol (N.B., aplysiatoxin and debromoaplysiatoxin possess phenol moieties), quinone, phloroglucinol, resorcinol, aniline, benzidine, pyrrole, uric acid, and other substances tested (Adams, C. W. M., *J. Clin. Path.,* 10:56–62, 1957) did not provide a blue coloration upon DMAB staining.

It is an object of the subject invention to provide a method for identifying certain indoles in biological materials.

A further object of the invention is to provide a relatively permanent biological stain for certain types of indoles.

SUMMARY OF THE INVENTION

The present invention provides a method for the histological staining of indoles. The method can be used on various strains of the "stinging seaweed" *Microcoleus lyngbyaceus* by the DMAB-AFB staining technique described below. The tissues are stained using the modified DMAB technique and then are counterstained using the Ziehl-Neelsen acid fast bacilli stain resulting in a relatively permanent histological stain for certain types of indoles (NB: the Fite acid fast bacillus stain is not satisfactory for this).

DETAILED DESCRIPTION OF THE INVENTION AND EXAMPLES

Figure 1:
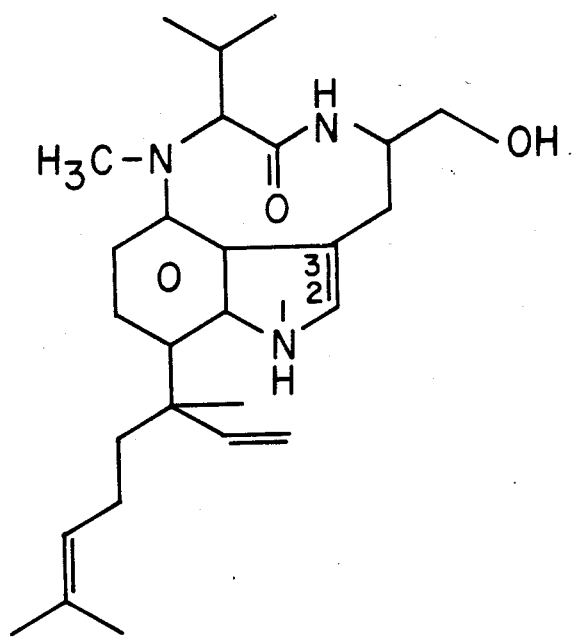

The blue-green algal organism *Microcoleus lyngbyaceus* (formerly *Lyngbya majuscula*) was identified grossly and microscopically (Grauer, F. H. and Arnold, H. L. Jr., *Arch. Derm.*, 84:720–732, 1961; Sims, J. K. et al., *Hawaii Med J.*, 40:243–248, 1981; Revision of the Classification of the Oscillatoriaceae by F. Drouet, Monograph 15, Academy of Natural Sciences of Philadelphia, Fulton Press, Lancaster, Pa., pp. 224–308, 338–341, 1968) for specimens collected at Kahala Beach (Oahu), Kaneohe Bay (Oahu), Kohala (Hawaii), Lahaina (Maui), and Buffalo Beach (Punaluu, Oahu) in the Hawaiian Islands.

The specimens were placed into 10% formalin. All specimens were identified grossly and microscopically for wet, fresh, dry or formalin-fixed preparations, with other adherent seaweeds being removed prior to embedding in paraffin blocks. The tissues were sectioned for histological staining and taken to alcohol then stained using (1) hematoxylin and eosin (i.e., H & E), (2) p-dimethylaminobenzaldehyde (DMAB) (Adams, C. W. M., *J. Clin. Path.*, 10:56–62, 1957; *Theory and Practice of Histological Techniques*, Ed. J. D. Bancroft and A. Stevens, N.Y: Churchill Livingstone, p. 115, 1977), as modified, and (3) DMAB-AFB (i.e., modified DMAB followed by Ziehl-Neelsen acid fast bacilli stain).

The 1957 p-dimethylaminobenzaldehyde (DMAB) indole stain of Adams was modified as follows:

(1) The tissue sections, were taken to alcohol and then "celloidinized" in about 0.5–1.5% collodion, rather than celloidin, to affix the tissue sections to the slides.

(2) The sections were placed in DMAB solution (i.e., p-dimethylaminobenzaldehyde solution, made by dissolving about 5 grams of pDMAB in 100 ml of concentrated hydrochloric acid), for 3–15 minutes, staining advantageously 10 minutes, rather than for 1 minute.

(3) The sections were transferred to a nitrite solution (i.e., about 1 gram of sodium nitrite is dissolved in 100 ml of concentrated hydrochloric acid). A yellow or yellow-brown precipitate can develop from this fuming acid mixture, so the solution should be stirred for 1 minute prior to use.

(4) The sections were rinsed in tap water for approximately 30 seconds.

(5) The sections were rinsed in acid alcohol for about 15 seconds.

(6) The sections were dehydrated through alcohols, cleared in xylene, and mounted using modern mounting media rather than DPX (DPX can be used).

The sections were counterstained using a standard Ziehl-Neelsen histological stain. At this point, the sections were referred to as having been DMAB-AFB stained. The Ziehl-Neelsen acid-fast bacilli stain is described as follows:

(1) The tissue sections were dewaxed in xylene and hydrated through graded alcohols to water.

(2) The sections were flooded with carbol fuchsin (prepared by dissolving about 1 g of basic fuchsin in 10 ml of absolute alcohol, and adding 100 ml of about 5% aqueous phenol solution, and after mixing well filtering prior to use) and heated to steaming (by intermittent flaming) for about 15 minutes or stained in a coplin jar at 56°–60° C. in an oven or water bath for about 30 minutes commercial Ziehl-Neelsen stain preparations can be used.

(3) The sections were rinsed in distilled water.

(4) The sections were differentiated in about 1% acid alcohol for about 10 minutes.

(5) The sections were rinsed in 25% aqueous sulphuric acid.

(6) The sections were placed in 25% aqueous sulphuric acid for 3 minutes or longer until the section is decolorized.

(7) The sections were washed in running tap water for at least 3 minutes.

(8) The sections were counterstained lightly in acidified methylene blue (about 0.25% methylene blue in 1% acetic acid) for $\frac{1}{2}$ to 1 minute.

(9) The sections were rinsed in tap water.

(10) Then the sections were dehydrated, differentiated in alcohols, cleared and mounted.

In the DMAB-AFB staining technique, the tissues are stained using the modified DMAB technique and then are counterstained using the Ziehl-Neelsen acid fast bacilli stain. Using the DMAB-AFB stain, DMAB-staining indoles are a deep red-purple or a deep purple. Although the DMAB preparation utilized above appeared to be a histochemical stain (i.e., provided best results when read promptly upon preparation, with stain color intensity substantially diminishing over days), the DMAB/AFB preparation appears to be a relatively "permanent" stain in terms of color-fastness and preservation of clarity.

The following volume of staining was conducted in terms of numbers of microscope slides, as reported on herein:

| Stain | Number of Microscope slides |
| --- | --- |
| H & E | 6 |
| DMAB (1 minute stain) | 3 (plus 2 human pancreas controls) |
| DMAB (3 minute stain) | 6 (plus 3 human pancreas controls) |
| DMAB (10 minute stain) | 18 (plus 6 human pancreas controls) |
| DMAB (solution over 24 hours old) | 6 (N.B., very poor staining resulted) |
| DMAB-AFB | 6 (plus AFB controls and human pancreas DMAB controls) |
| AFB | 3 (plus 1 AFB control). |

Using the modified DMAB (Adams, C. W. M., *J. Clin. Path.*, 10:56–62, 1957; *Theory and Practice of Histological Techniques*, Ed. J. D. Bancroft and A. Stevens, N.Y.: Churchill Livingstone, p. 115, 1977), staining method for indoles and the DMAB-AFB stain for indoles, as described herein, the Kahala Beach, Lahaina, and Buffalo Beach specimens were indole positive, the Kohala specimen was indole negative, and the Kaneohe Bay specimen was very slightly indole positive at the algal filament tips. Indole positivity for the p-dimethylaminobenzaldehydenitrite (DMAB) stain consists of a light blue color (Adams, C. W. M., *J. Clin. Path.*, 10:56–62, 1957; *Theory and Practice of Histological Techniques*, Ed. J. D. Bancroft and A. Stevens, N.Y.: Churchill Livingstone, p. 115, 1977), this correlating with a strong purple color for the DMAB-AFB stain. Indole negativity (e.g., absent or unstainable concentrations of 2- or 3- open indole derivatives) for the algal filaments was reflected in a light-to-bright-yellow coloration.

The hematoxylin and eosin (H&E) stain was utilized to demonstrate the morphology of the *Microcoleus lyngbyaceus* under H & E staining. The primary algal filament was shown to consist of a fairly homogeneous diameter tubule in which the disks are stacked as "coins are held in a conductor's change holder", (Grauer, F. H. and Arnold, H. L. Jr., *Arch. Derm.*, 84:720–732, 1961), or coins in a bank coin wrapper (Sims, J. K. and Zandee van Rillard, R. D., *Hawaii Med. J.*, 40:243–248, 1981). These trichromes may be 3.5-80 microns in diameter (Revision of the Classification of the Oscillatoriaceae by F. Drouet, Monograph 15, Academy of Natural Sciences of Philadelphia, Lancaster, Pa.: Fulton Press, pp. 224-308, 338-341, 1968). The filaments, or trichromes, for the specimens examined generally were coated with a thick homogeneous mucus, (Revision of the Classification of the Oscillatoriaceae by F. Drouet, Monograph 15, Academy of Natural Sciences of Philadelphia, Lancaster, Pa.: Fulton Press, pp. 224-308, 338-341, 1968), which along the edge opposite to the algal filament was speckled in places with ovoid diatoms, microorganisms, and debris. It was noted for the algae that the heavily indole positive areas were not infrequently basophilic on the hematoxylin and eosin (H&E) stained tissues. In some specimens vacuoles were seen within the filaments, particularly in the more disrupted fragmented specimens.

The DMAB stain was utilized to see if lyngbyatoxin A in toxic varieties of *Microcoleus lyngbyaceus* would be stained. Since the Kaneohe Bay variety of *M.lyngbyaceus* had been previously reported to be nontoxic, (Banner, A. H., *Hawaii Med. J.,* 19:35-36, 1959) the Kaneohe Bay specimen was collected to function as an indole, negative control. Lyngbyatoxin A, (Cardellina, J. H. II et al., *Science,* 204:193-195, 1979), was discovered in a variety of *M. lyngbyaceus* (i.e., *Lyngbya majuscula* Gomont) from Kahala Beach, Oahu, so a specimen was collected from this area to serve as an indole positive control. The Kohala, Hawaii specimen was that obtained from a patient who sustained escharotic stomatitis from *M. lyngbyaceus,* this poisoning having been reported previously (Sims, J. K. and Zandee van Rillard, R. D., *Hawaii Med. J.,* 40:243-248, 1981). Prospectively it was not known how the specimens would actually stain, particularly for the Kohala, Lahaina, and Buffalo Beach specimens. The Kahala Beach specimen stained indole positive and did serve as an indole positive control. The Kaneohe Bay specimen stained indole positive so faintly at some filament tips to function as an indole negative control for the stain, the Kaneohe Bay and the Kohala specimens being utilized in this regard. The Lahaina, Maui *M. lyngbyaceus* specimen and the Buffalo Beach (Punaluu, Oahu) specimen were indole positive, whereas the toxic Kohala, Hawaii specimen was indole negative for the stain (i.e., specimen may contain aplysiatoxin, debromoaplysiatoxin, indoles which do not react with the stain, and/or other toxin(s)). These staining patterns were also seen for the DMAB-AFB stain, although indole positivity was characterized by a purple color and indole negativity by a blue, green, or blue-green color in regard to *M. lyngbyaceus* filaments.

The mucus and the diatoms were associated with numerous specimens, including the Kaneohe Bay and the Lahaina specimens. In general, the indole-positive DMAB stained algal filaments were blue in coloration, whereas the indole-negative filaments were bright yellow. For the DMAB-AFB stain the DMAB indole-positive algal specimens had trichrome disks which were dark red-purple in coloration with blue trichrome sheaths, whereas the DMAB indole-negative trichromes were blue.

Staining of the specimens for one minute with the DMAB stain produced a blue coloration for the indole positive algae and pancreas controls. The intensity of the blue coloration increased upon three minute staining and even more for 10 minute staining of indole positive algae, however the intensity of the staining of the pancreas control did not substantially increase relative to 1-3 minute staining. This suggested that the algae may have a larger reservoir of DMAB-stainable groups than the pancreas controls, and might function as a more sensitive control. The DMAB indole-positive algal filament blue coloration was noted in a number of preparations to change to blue-grey, grey, and yellow-brown-black colors, including structural degradation into granules. This indicated the technique to be more of a histochemical technique rather than one that would render a relatively permanent slide. Utilization of the DMAB-/AFB technique rendered histological slides which correlated positively with the DMAB results as to indole staining, demonstrated clarity of structure, and which were relatively permanent in regard to colorfastness and clarity.

While not seeking to limit the subject invention, the structures of the stains are believed to be those discussed below.

Utilization of the DMAB stain, as modified, provided a blue color for *Microcoleus lyngbyaceus* specimens from Kahala Beach (Oahu), Lahaina (Maui), and Buffalo Beach (Punaluu, Oahu) particularly, a yellow color for Kohala (Hawaii) specimens, and a yellow color with faintly blue filament tips for specimens from Kaneohe Bay (Oahu), pancreas controls for the stain being blue. This suggested the possibilities of 2- or 3-indole compounds in the indole-positive algal specimens (as free amines), the possibilities of the formation of 2- or 3-indole compounds during the DMAB-nitrite histochemical reaction process, and the possibility that lyngbyatoxin A could undergo opening of the lactam ring to form the indole compound required to react with the DMAB to form the carboline which was projected to give the blue 3-indolyl histochemical product (like tryptophan) under the old hypothesis as to the chemical reaction for DMAB (Adams, *J. Clin. Path.,* 10:56-62, 1957). More recently it has been hypothesized that the aldehyde DMAB reacts at the 2- or 3-position of the indole nucleus directly to form the specific pigmented reaction products, and it would be possible for either "opened" or regular lyngbyatoxin A to react with DMAB under this newer hypothesis to generate a (pigmented) reaction product (*Properties and Reactions of Indoles* by W. A. Remers, in Houlihan, W. J. (ed): Indoles (Part 1), N.Y.: Wiley-Interscience, pp. 105-107, 1972).

Figure 2:
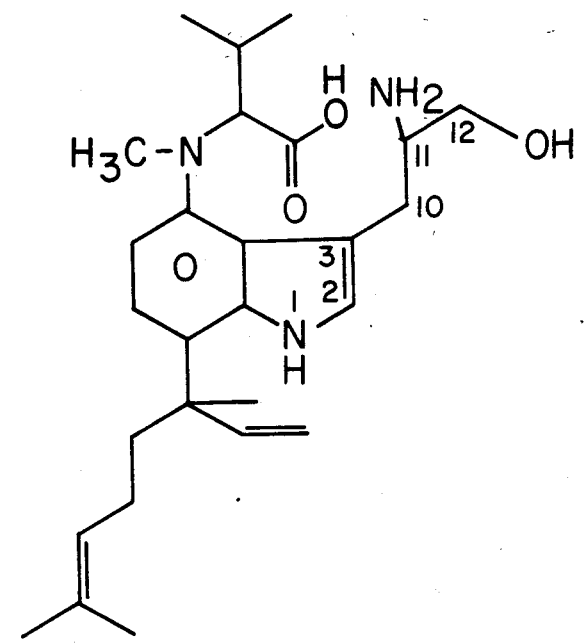
Figure 6:
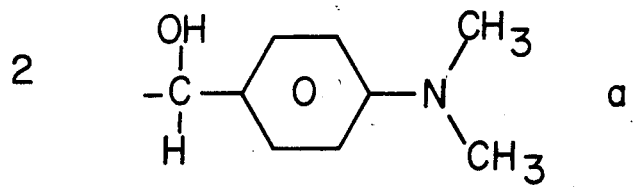
Figure 6:
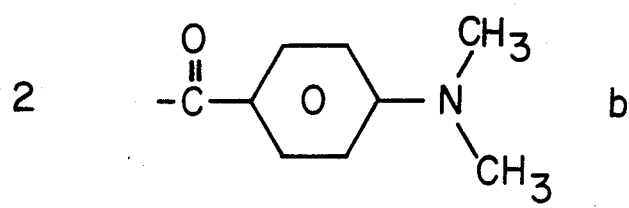
Figure 6:
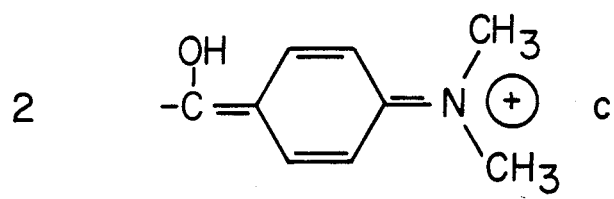
Figure 6:
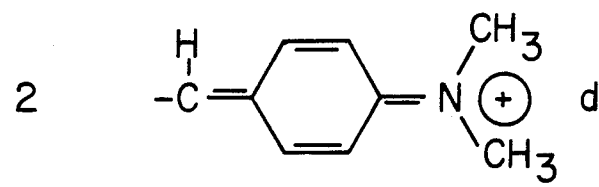
Figure 6:
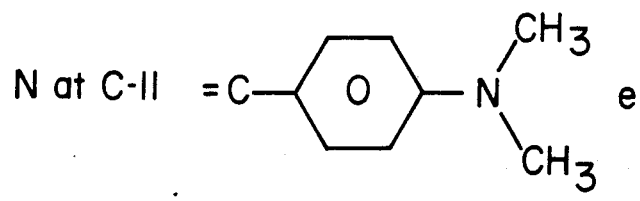

Opened lyngbyatoxin A (OLA) (FIG. 2) and lyngbyatoxin A (FIG. 1) may react at the 2-position of the indole nucleus to form pigments (refer to FIG. 6, adducts a-d). The formation of a pigment by reacting lyngbyatoxin a and DMAB, is favored as the DMAB portion of the molecule (FIG. 6, adduct c) has the potential for being positively charged as a salt, thereby rendering the molecule water soluble. Further, with the addition of DMAB at the 2-position, the DMAB portion would be able to resonate with the indole ring. In addition, the anionic and cationic forms of opened lyngbyatoxin A (FIG. 2) may react similarly to form pigments (refer to FIG. 6, adducts a-d). The formation of pigment by reacting the cationic form of opened lyngbyatoxin a and DMAB is favored (FIG. 6, adduct c), due to the presence of a high concentration of hydrochloric acid in the staining media so that ring opening and the formation of a protonated amino group is favored. The indole nucleus of lyngbyatoxin A (FIG. 1) may lose a proton from the nitrogen and react with DMAB to produce pigments (refer to FIG. 6 for adducts a-d), polymers, and also decarboxylation and deamination products also as the aldehyde.

Figure 3:
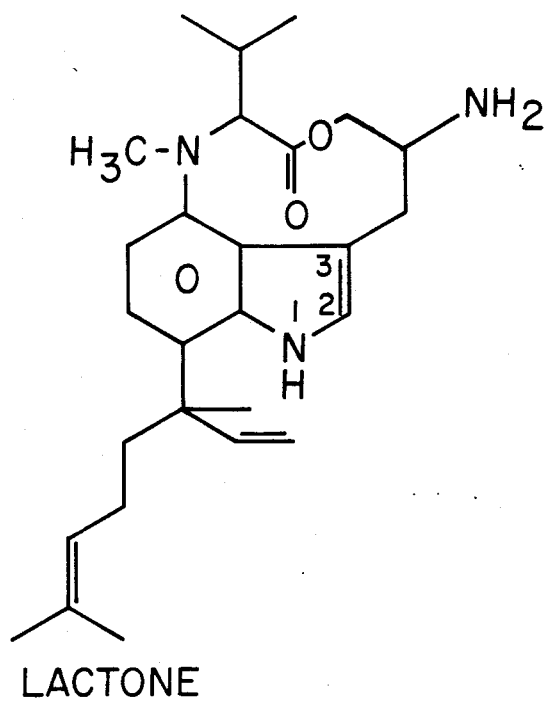

The anionic form of opened lyngbyatoxin A (FIG. 2) may react with DMAB at the free primary amine group to form a pigment (FIG. 6, adduct e), as a schiff base. Its deprotonated structure FIG. 2 also may form pigments. Further, opened lyngbyatoxin (FIG. 2) may undergo self-condensation to form a lactone (FIG. 3) that reacts with DMAB at the 2-position of the indole nucleus to form pigments (refer to FIG. 6, adducts a-d). Further, DMAB may react at the free primary amine group (refer to FIG. 6 adduct) to form additional pigments (refer to FIG. 6, adducts a-d). Also, two or more molecules of opened lyngbyatoxin A (FIG. 2) may react at the free hydroxy or primary amine group to form polyesters or polyamides (refer to FIG. 7, adducts f and g) or react with DMAB at the 2-position of the indole nucleus. One molecule of lyngbyatoxin A may react with DMAB at the 2-position of the indole nucleus.

Figure 5:
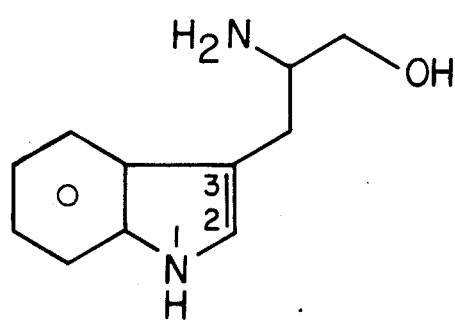

The tryptophan nucleus (FIG. 5) may also react with DMAB at the 2-position to form pigments (refer to FIG. 6, adducts a-d). Additional pigments may be produced from the anionic and cationic forms and deprotonated forms.

Figure 4:
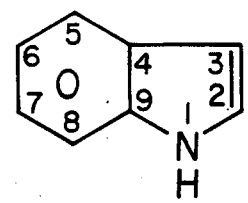

The indole nucleus (FIG. 4), its substituted and unprotonated forms may react with DMAB at the 2- or 3-position to form pigments (refer to FIG. 6, adducts a-d for the 2-position). Further, two molecules of the indole nucleus may react with DMAB and Ziehl-Neelsen (AFB) stain at the 2- or 3-position (refer to FIG. 6, adducts a-d for the 2-position and FIG. 8, adducts h-i for the indole nitrogen). Positions 1-3 and 5-8 on the molecule illustrate the potential reactive sites for DMAB and AFB stain pigment (e.g. basic fuchsin, pararosaniline, rosaniline) addition.

The indole nucleus in lyngbyatoxin A can act as a base and initially form a salt. The 2 electrons forming the double bond between the carbons at positions 2 and 3 on the ring may shift to the nitrogen, creating a negative charge enhancing salt formation, with the addition of a molecule of rosaniline, p-rosaniline or basic fuchsin from the AFB stain at the 1-position (FIG. 8, adduct h) (*Principle and Techniques of Histochemistry* by Henry Troyer, Boston: Little, Brown and Co., pp. 385, 389 and 396 (1980)). Subsequently, DMAB derivatives may form at the 2-position and the chloride ion from the hydrochloric acid in solution or from the basic fuchsin present as a salt forms a bond at the 3-position. Similar reactions may occur for tryptophan and other indoles.

Figure 8:
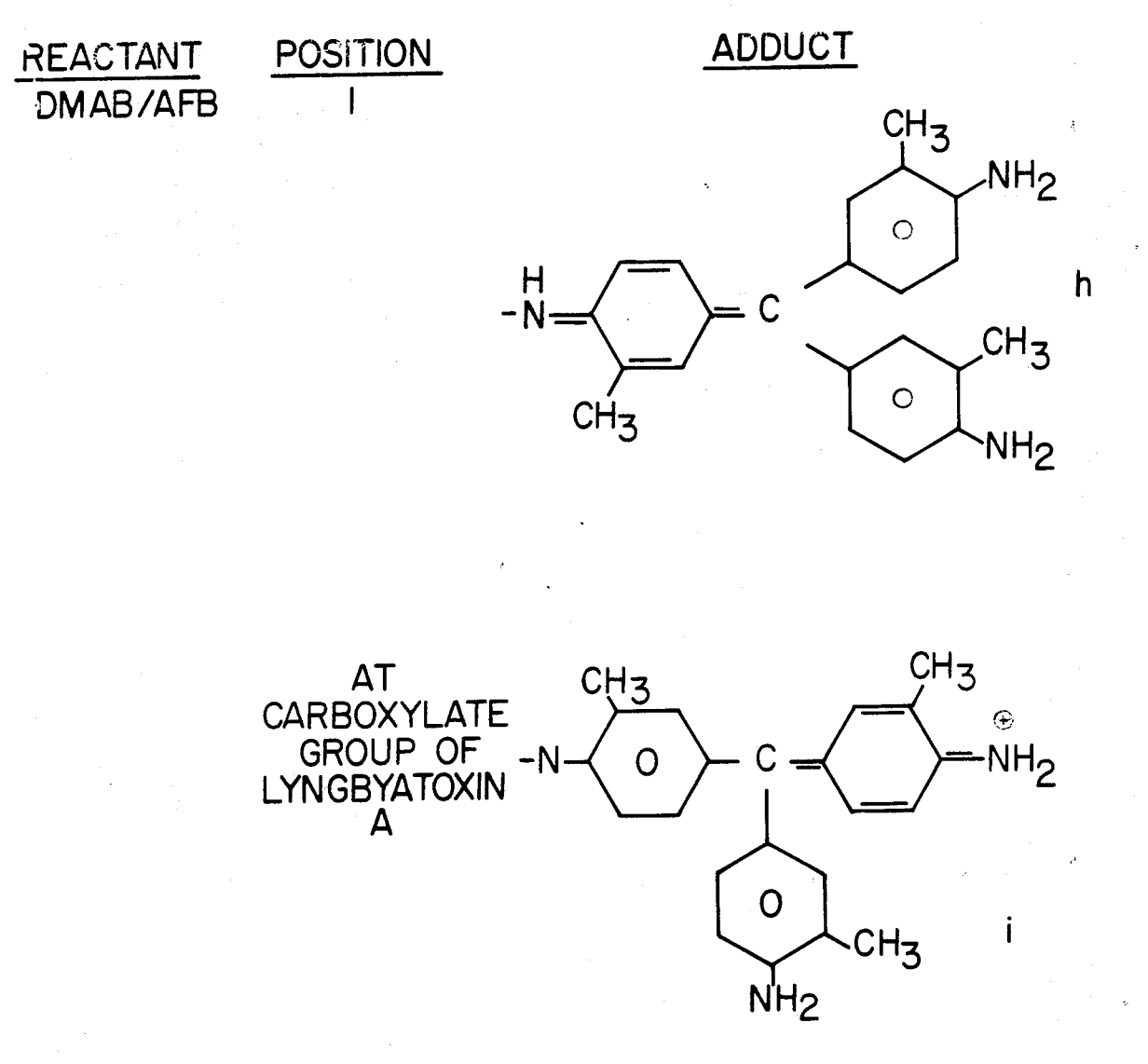

A molecule of rosaniline, p-rosaniline or a basic fuchsin may react with the free carboxylic acid group of lyngbyatoxin A, with DMAB derivatives forming at the 2-position (FIG. 8, adduct i). The primary amine group of the rosaniline, p-rosaniline or basic fuchsin may further react with one or more lyngbyatoxin A molecules, or other indoles, and polymerize.

Lyngbyatoxin A has olefinic side chains, a valine (amino acid) moiety, a potential free carboxylic acid group (upon opening of the lactam ring), a hydroxyl group, a potential free primary amine group (upon opening the lactam ring), a saturated aliphatic side chain, an indole nucleus, and a tryptaminyl element (upon opening the lactam ring). It was felt to be desirable to stain for the indole moiety using the modified DMAB stain, and to more specifically identify the lyngbyatoxin A or its derivatives by also staining for one or more side chains. In considering the olefin side chain it was elected to utilize the Ziehl-Neelsen acid fast bacilli (AFB) stain. Modified DMAB staining followed by Ziehl-Neelsen staining (as a counterstain) was utilized and it effected a deep purple color to the disks in the trichromes of the Kahala Beach, Lahaina (Maui), and Buffalo Beach specimens. It is possible that the DMAB staining process' acid-nitrite treatment oxidizes the double bond and generates an aldehyde to react with the AFB stain since the AFB stain clearly reacts with aldehyde groups (i.e., when the Ziehl-Neelsen AFB stain was reacted in this study with a solidified mixture of gelatin and p-dimethylaminobenzaldehyde, a bright red colored streamered section resulted).

In summary, DMAB and DMAB-AFB tissue stains can be utilized to at least qualitatively demonstrate 2- and/or 3-indoxyl (i.e. "indole") compounds. The DMAB-AFB stain is particularly invaluable in its deep red-purple or purple readily visible staining product when positive and its relatively "permanent" character. Some degeneration of the deep purple into the Ziehl-Neelsen AFB stain red pigmentation is seen after a number of months for some slides. It is recommended, then, that the slides for DMAB-AFB staining be reviewed within a few days of staining and photomicrographs taken promptly in order to obtain the most optimal results. Often staining remained intact for over three to four years for the DMAB-AFB stain.

The DMAB-AFB stain may be used in staining other tissues, particularly those bearing indoles, such as the nervous system, lung, and gastrointestinal tract.

While the present invention has been illustrated by detailed descriptions of preferred embodiments thereof, it will be obvious to those skilled in the art that various changes in form and detail can be made therein without departing from the true scope of the invention. For that reason, the invention must be measured by the claims appended hereto.

What is claimed is:

1. A method of staining indoles in samples comprising the steps of:
    (1) staining the sample using a modified DMAB technique which technique comprises,
        (a) treating tissue sections in 0.5-1.5% collodion,
        (b) placing the sections in DMAB solution, and
        (c) transferring the sections to a nitrite solution comprising sodium nitrite in concentrated hydrochloric acid, and
    (2) counterstaining the stained sample of step (1) using the Ziehl-Neelsen acid fast bacilli stain,
    whereby samples containing indoles are stained.

2. A method as in claim 1, wherein in step (b) the DMAB solution comprises about 5 g. DMAB in about 100 ml of hydrochloric acid.

3. A method as in claim 1 wherein directly after step (b) is the step of transferring the sections to a nitrite solution.

4. A method as in claim 1 further comprising step 2 the step of treating the sections with methylene blue.

5. A method as in claim 1 further comprising before step 2 the steps of:
rinsing the sections with water
rinsing the sections in acid alcohol
dehydrating the sections
clearing the sections in xylene, and
mounting the sections using modern mounting media.

6. A DMAB and AFB stain pigment produced by the method of claim 1.

* * * * *